United States Patent [19]

Cordier

[11] Patent Number: 4,590,309
[45] Date of Patent: May 20, 1986

[54] PROCESS FOR THE PREPARATION OF PERFLUOROALKANOLS

[75] Inventor: Georges Cordier, Francheville, France

[73] Assignee: Rhone-Poulenc Specialites Chimiques, Courbevoie, France

[21] Appl. No.: 727,621

[22] Filed: Apr. 30, 1985

Related U.S. Application Data

[63] Continuation of Ser. No. 596,939, Apr. 5, 1984, abandoned.

[30] Foreign Application Priority Data

May 6, 1983 [FR] France ............... 83 07569

[51] Int. Cl.$^4$ ............. C07C 29/136; C07C 31/40
[52] U.S. Cl. ......................... 568/842; 502/223; 502/230; 502/325; 502/331
[58] Field of Search ............................... 568/842

[56] References Cited

U.S. PATENT DOCUMENTS

| | | | |
|---|---|---|---|
| 2,862,977 | 12/1958 | Schreyer | 568/842 |
| 3,318,662 | 5/1967 | Pauling | 423/522 |
| 3,390,191 | 6/1968 | Anello et al. | 568/842 |
| 3,663,629 | 5/1972 | Fischer | 568/842 |
| 4,273,947 | 6/1981 | Novotny | 568/842 |
| 4,396,784 | 8/1983 | Johnson et al. | 568/842 |

FOREIGN PATENT DOCUMENTS 7031913 6/1971 France .

*Primary Examiner*—J. E. Evans
*Attorney, Agent, or Firm*—Finnegan, Henderson, Farabow, Garrett & Dunner

[57] ABSTRACT

A process for preparing perfluoroalkanols by hydrogenation of the corresponding aliphatic perfluoroacids. An acid of the formula:

$$C_nF_{2n+1}COOH$$

in which n is greater than or equal to 1, is reacted with hydrogen, in the presence of a catalyst based on ruthenium, rhodium, iridium or platinum, under a total pressure of between 1 and 50 bar and in the presence of at least one additive chosen from the group comprising the halide anions and the metal cations of columns IB, IIB, IVA, VA and VB of the periodic table of the elements.

31 Claims, No Drawings

PROCESS FOR THE PREPARATION OF PERFLUOROALKANOLS

This application is a continuation of application Ser. No. 596,939, filed April 5, 1984, abandoned.

The present invention relates to a process for the preparation of perfluoroalkanols; it relates more particularly to a process for the preparation of perfluoroalkanols by hydrogenation of the corresponding perfluorinated aliphatic acids.

French Patent Application 70/31,913, published under No. 2,060,357, is known in the prior art and describes the preparation of 1,1-dihydroperfluoroalkanols corresponding to the general formula $C_nF_{2n+1}CH_2OH$, in which $n \geq 3$, by the hydrogenation of acids or esters of the formula $C_nF_{2n+1}COOR$, in which R represents a hydrogen atom or an alkyl radical and in which $n \geq 3$, in the presence of a ruthenium-based catalyst.

In this process, the hydrogenation is carried out in the presence of 4 to 1000% by weight of water, relative to the acid or ester, and under a high temperature and a high hydrogen pressure. The temperature is between 80 and 240° C. and the initial hydrogen pressure varies between 5 and 700 kgp/cm².

This process makes no provision for the possibility of using trifluoroacetic acid ($n=1$) to obtain trifluoroethanol.

The preparation of trifluoroethanol is again not envisaged in U.S. Pat. No. 2,862,977, which describes the preparation of 1,1-dihydroperfluoroalkylalcohols of the formula $C_nF_{2n+1}CH_2OH$ ($n>1$) by the hydrogenation of the corresponding acid under a pressure of at least 1000 p.s.i. (70 bar) and at a temperature above 150° C., in the presence of a ruthenium-based catalyst.

U.S. Pat. No. 4,273,947 is also known, which describes a process for the hydrogenation of trifluoroacetic acid ($CF_3COOH$) in which this acid is brought into contact with hydrogen in the liquid phase, in the presence of a supported or unsupported catalyst based on rhodium or iridium, under a pressure of 5 to 15 atmospheres and at a temperature of 50 to 150° C.

By studying the processes of the prior art which have been analyzed above, the inventor has found that, in the case of the hydrogenation of trifluoroacetic acid, secondary hydrogenolysis reactions develop, giving rise to gaseous products such as HF, $CF_3$—$CH_3$, $CH_3$—$CH_3$ and $CH_4$, which accumulate in the reactor and block the hydrogenation reaction. These secondary reactions also exist in the case of acids having a larger number of carbon atoms, but, in this case, the by-products have a much lower vapor pressure and do not have such an adverse effect on the hydrogenation reaction. The inventor has furthermore found that these secondary reactions are more significant in the case of a ruthenium-based catalyst than in the case of a rhodium-based catalyst.

The inventor has now discovered a process making it possible to minimize and even to eliminate these secondary reactions, which are also the cause of a considerable loss of yield.

The invention therefore relates to a process for the preparation of perfluoroalkanols by hydrogenation of the corresponding aliphatic perfluoroacids, which comprises reacting an acid of the formula:

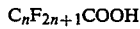

$$C_nF_{2n+1}COOH$$

in which n is greater than or equal to 1, with hydrogen, in the presence of a catalyst based on ruthenium, rhodium, iridium or platinum, under a total pressure of between 1 and 50 bar and in the presence of at least one additive chosen from the group comprising the halide anions and the metal cations of columns IB, IIB, IVA, VA and VB of the periodic table of the elements.

It is preferred to use a quantity of additive of between 0.001 and 10 gram atoms per gram atom of catalyst metal, i.e. per gram atom of ruthenium, rhodium, iridium or platinum. Even more preferably, this quantity is between 0.01 and 1 gram atom.

The metal cation is preferably chosen from the cations of the metals of columns IB, IIB, IVA, VA and VB of the periodic table of the elements. Even more preferably, it is derived from the following metals: Cu, Ag, Cd, Hg, Sn, Pb, Sb, Bi and Ta. It is very particularly preferred to use the cations derived from Pb and Ta.

The metal cation is preferably used in the form of a salt or an oxide. Examples which may be mentioned are: tantalum pentoxide, $Ta_2O_5$, bismuth oxide, $Bi_2O_3$, tin oxide, $SnO_2$, the acetates and trifluoroacetates of $Pb^{2+}$, $Cu^{2+}$, $Hg^+$ and $Cd^{2+}$, or carbonates ($Ag_2CO_3$) and the sulfates of $Cu^{2+}$ and $Cd^{2+}$.

The halide anion is preferably used in the form of the corresponding hydrogen acid (HCl, HF, HBr and HI), the halide of the abovementioned metals of columns IB, IIB, IVA, VA and VB or the halide of the alkali metals and alkaline earth metals of columns IA or IIA of the periodic table. Examples which may be mentioned are: the fluorides, chlorides, bromides and iodides of lithium, sodium, potassium, calcium and magnesium.

It is very particularly preferred to use the hydrogen acids.

The invention is particularly suitable for carrying out the hydrogenation reaction under a pressure of between 5 and 30 bar.

The catalysts used within the scope of the process according to the invention can be in the form of the metal itself or in the form of an oxide or a salt, or a mixture of these. Furthermore, they may or may not be deposited on a support.

It is possible to use any support which is inert under the reaction conditions, such as charcoal, silica or alumina. The use of charcoal will be very particularly preferred.

The quantity of metal deposited on the support is preferably between 0.1 and 20% by weight and more preferably between 1 and 10%.

Examples of catalysts which may be mentioned are: ruthenium, rhodium, iridium or platinum in the form of the metal, their oxides, hydroxides and salts with acids (nitrates, sulfates and acetates) and mixtures of these, if appropriate deposited on charcoal or silica.

In a very particularly preferred embodiment, rhodium metal deposited in a proportion of 5% on charcoal is used.

The reaction is preferably carried out at a temperature of between 20° and 200° C. Even more preferably, the temperature is between 70° and 150° C.

The quantity of catalyst used (expressed in % of the metal) is preferably less than 10% by weight, relative to the aliphatic perfluoroacid. Even more preferably, less than 2% of catalyst is used.

The reaction preferably takes place in the presence of a solvent. However, it is not excluded to carry out the reaction without a solvent. Water or an inert organic compound (for example an alkane) can be used. Water facilitates the use of catalysts which are generally sold moist.

The invention is particularly advantageous for obtaining trifluoroethanol by hydrogenation of trifluoroacetic acid. Other advantages and characteristics of the invention will become apparent on reading the examples which follow:

EXAMPLE 1

The following are introduced into a corrosion-resistant Hastelloy $B_2$ autoclave having a useful volume of 125 ml:

0.3 mol of trifluoroacetic acid 0.3 g of a catalyst consisting of 5% of Rh deposited on a charcoal of large specific surface area $\geq 900$ $m^2g^{-1}$ 0.018 g of tantalum pentoxide, i.e. a ratio Ta/Rh=0.6.

After the air has been removed by means of an inert gas such as nitrogen, and the nitrogen then replaced with hydrogen, the pressure in the reactor is brought to 45 bar and the reactor is heated to 120° C. The reaction starts while the temperature is rising and the consumption of hydrogen thus compensates for the pressure increase associated with the expansion of the gases. The hydrogen necessary for the reaction is then fed in continuously, the pressure being kept constant at 45 bar. The reaction stops after 2 hours 10 minutes.

After the enclosure has been cooled and degassed, analysis of the reaction mixture by VPC shows that the degree of conversion of the trifluoroacetic acid is 100% and the yield of trifluoroethanol is >99.5%. Analysis of the gases contained in the reactor makes it possible to calculate a yield of 0.3% of methane.

The yield of $CF_3CH_3$ and $C_2H_6$ is zero.

If no tantalum pentoxide is added, the yield of trifluoroethanol is now only 94% while the yield of $CF_3CH_3$ is 5% and that of $CH_4$ is 0.8%.

EXAMPLE 2

Example 1 is repeated, but 0.27 mg of lead acetate, $Pb(CH_3COO)_2\cdot 3H_2O$ is added instead of tantalum pentoxide, i.e. a ratio Pb/Rh=0.005. The reaction is stopped after 200 minutes. The degree of conversion of the trifluoroacetic acid is 97.5% and the yield of trifluoroethanol is 98%. The yield of $CF_3CH_3$ is 1.2% and that of methane is 0.06%.

EXAMPLE 3

Example 2 is repeated, 10 times the quantity of $Pb(CH_3COO)_2\cdot 3H_2O$ being introduced.

The reaction stops after 500 minutes. The degree of conversion of the trifluoroacetic acid is 96.5% and the yield of trifluoroethanol is 100%. There are no longer any heavy fluorinated gases and only traces of methane are found.

EXAMPLE 4

The reaction is carried out in the same reactor as in Example 1, but the following are introduced:

0.2 mol of trifluoroacetic acid 0.4 g of the 5% Rh/charcoal catalyst employed in Example 1

2.5 ml of water and no additive.

The reaction is carried out in the manner stated in Example 1, but at 150° C./total pressure of 20 bar. It stops after 85 minutes. The degree of conversion of the trifluoroacetic acid is 99.3%. The yield of trifluoroethanol is 93.5%.

Analysis of the gases in the enclosure makes it possible to calculate a yield of 5% for $CF_3CH_3$, 0.4% for $CF_2HCH_3$, 0.4% for $C_2H_6$ and 0.4% for $CH_4$, i.e. a total yield of by-products of 6.2%.

EXAMPLE 5

Example 4 is repeated, 20 mg of copper acetate, $Cu(CH_3COO)_2\cdot H_2O$, being added to the reaction medium, i.e. a ratio $Cu^{2+}$/Rh of 0.5. The reaction stops after 2 hours at 150° C. and under a total pressure of 20 bar.

The degree of conversion of the trifluoroacetic acid is 48.6% and the yield of trifluoroethanol is 97.5%.

Analysis of the gases makes it possible to calculate a yield of $CF_3CH_3$ of 2.1% while those of $CF_2HCH_3$, $C_2H_6$ and $CH_4$ are each equal to 0.2%.

EXAMPLE 6

Example 5 is repeated, the cupric acetate being replaced with 0.003 g of stannous sulfate, $Sn(SO_4)$, i.e. $Sn^{2+}$/Rh:0.07. After a reaction time of 6 hours 50 minutes at 150° C. and under a pressure of 20 bar, the reaction stops. The degree of conversion of the trifluoroacetic acid is 94% while the yield of trifluoroethanol is 97.2%.

Analysis of the gases shows a yield of $CF_3CH_3$ of 2.1% and traces of $CF_2HCH_3$ (0.05%) and of ethane (0.15%).

EXAMPLE 7

Example 5 is repeated, 0.016 ml of an aqueous solution of HI containing 1 mol/liter being added to the reaction medium.

The reaction stops after 355 minutes. The degree of conversion of the trifluoroacetic acid is 96.3%. The yield of trifluoroethanol is 96%. Analysis of the gases makes it possible to calculate:

| yield of $CF_3CH_3$ | 3% |
| yield of $CF_2HCH_3$ | 0.2% |
| yield of $C_2H_6$ | 0.3% |
| yield of $CH_4$ | 0.3% |

EXAMPLE 8

Example 5 is repeated, 0.16 ml of an aqueous solution of HCl containing 1 mol/liter being added to the medium.

After a reaction time of 70 minutes, analysis of the reaction medium indicates that the degree of conversion of the trifluoroacetic acid is 40% and the yield of trifluoroethanol is 98.5%. Analysis of the gases makes it possible to calculate:

| yield of $CF_3CH_3$ | 1% |
| yield of $CF_2HCH_3$ | 0.3% |
| yield of $C_2H_6$ | 0% |
| yield of $CH_4$ | 0.2% |

EXAMPLE 9

The reaction is carried out in the manner stated in Example 1, but the catalyst is now ruthenium deposited in a proportion of 5% on a charcoal of large specific surface area ($\geq 900$ m²/g) and the following are introduced:

| trifluoroacetic acid | 0.2 mol |
|---|---|
| 5% Ru/C catalyst | 2.5 g |
| H₂O | 7.5 g |

The reaction is carried out at 150° C. and under a total pressure of 50 bar. It stops after 30 minutes.

Analysis of the reaction mixture indicates that the trifluoroacetic acid has been totally converted. The yield of trifluoroethanol is 90.5%. Analysis of the gas phase indicates the following yields:

| $CF_3CH_3$ | 6.7% |
|---|---|
| $CHF_2CH_3$ | 0% |
| $C_2H_6$ | 1.9% |
| $CH_4$ | 0.9% |

EXAMPLE 10

Example 9 is repeated with half the quantity of the same catalyst, 0.481 g of cadmium sulfate (3CdSO₄.8-H₂O) being added to the medium, i.e. a ratio Cd/Ru of 4.

The reaction stops after 275 minutes. The degree of conversion of the trifluoroacetic acid is 94.5% while the yield of trifluoroethanol is 95.3%. Analysis of the gas phase makes it possible to calculate the following yields:

| $CF_3CH_3$ | 2.6% |
|---|---|
| $CF_2HCH_3$ | 0.8% |
| $C_2H_6$ | 0.8% |
| $CH_4$ | 0.3% |

EXAMPLE 11

Example 10 is repeated, 0.195 g of silver sulfate, Ag₂SO₄, being added to the medium in place of the cadmium sulfate, i.e. a ratio Ag/Ru=2.

The reaction stops after 90 minutes. The degree of conversion of the trifluoroacetic acid is 97% and the yield of trifluoroethanol is 93.5%.

Analysis of the gas phase makes it possible to calculate the following yields:

| $CF_3CH_3$ | 4.2% |
|---|---|
| $CF_2HCH_3$ | 0.65% |
| $C_2H_6$ | 1.0% |
| $CH_4$ | 0.3% |

EXAMPLE 12

Example 10 is repeated, the cadmium sulfate being replaced with antimony trioxide, Sb₂O₃ (0.091 g), i.e. a ratio Sb/Ru=1.

The reaction stops after 255 minutes. The degree of conversion of the trifluoroacetic acid is 52.5% and the yield of trifluoroethanol is 96.3%.

Analysis of the gas phase makes it possible to calculate the following yields:

| $CF_3CH_3$ | 2.45% |
|---|---|
| $CF_2HCH_3$ | 0.3% |
| $C_2H_6$ | 0.3% |
| $CH_4$ | 0.3% |

EXAMPLE 13

Example 10 is repeated, the cadmium sulfate being replaced with 0.155 g of mercurous sulfate, i.e. a ratio Hg/Ru=1.

The reaction stops after 150 minutes.

The degree of conversion of the trifluoroacetic acid is 52.5% and the yield of trifluoroethanol is 96.5%.

At the same time, the calculated yields for the gaseous by-products are:

| $CF_3CH_3$ | 2.25% |
|---|---|
| $CF_2HCH_3$ | 0% |
| $C_2H_6$ | 0.85% |
| $CH_4$ | 0.35% |

EXAMPLE 14

Example 10 is repeated, the cadmium sulfate being replaced with 47 mg of lead acetate, i.e. Pb/Ru=0.2.

The reaction stops after 450 minutes.

The degree of conversion of the trifluoroacetic acid is 97.9%. The yield of trifluoroethanol is 95.8% while the yields of gaseous by-products are:

| $CF_3CH_3$ | 2.6% |
|---|---|
| $C_2H_6$ | 1.3% |
| $CH_4$ | 0.3% |

EXAMPLE 15

Example 10 is repeated, the cadmium sulfate being replaced with 250 mg of hydrated cupric acetate, Cu(CH₃COO)₂. H₂O, i.e. a ratio Cu²⁺/Ru=2.

The reaction stops after 815 minutes.

The degree of conversion of the trifluoroacetic acid is 98.3% while the yield of trifluoroethanol is 97.1%.

The yields of gaseous by-products are:

| $CF_3CH_3$ | 2.0% |
|---|---|
| $C_2H_6$ | 0.55% |
| $CH_4$ | 0.3% |

EXAMPLE 16

Example 10 is repeated, the cadmium sulfate being replaced with 0.5 ml of an aqueous solution of HCl containing 0.1 mol/liter, and the reaction is carried out at 140° C. and under a pressure of 37 bar.

The reaction stops after 215 minutes.

The degree of conversion of the trifluoroacetic acid is 98.4%. The yield of trifluoroethanol is 94.5%.

The yields of gaseous by-products are:

| $CF_3CH_3$ | 3.9% |
|---|---|
| $C_2H_6$ | 1.9% |
| $CH_4$ | 0.35% |

What is claimed is:

1. A process for the preparation of perfluoroalkanols by hydrogenation of the corresponding aliphatic perfluoroacids, which comprises reacting an aliphatic perfluoroacid of the formula:

$$C_nF_{2n+1}COOH$$

in which n is greater than or equal to 1, with hydrogen, in the presence of a catalyst based on a metal selected from the group consisting of ruthenium, rhodium, iridium and platinum, under a total pressure of between 1 and 50 bar and in the presence of at least one additive selected from the group consisting of a halide anion and a cation of any metal of columns IB, IIB, IVA, VA and VB of the periodic table of the elements, wherein said additive is present in an amount from 0.001 to 10 gram atoms per gram atom of catalyst metal.

2. The process of claim 1, wherein the quantity of additive is between 0.01 and 1 gram atom.

3. The process of claim 2, wherein the anion is used in the form of a corresponding hydrogen acid or a halide of any metal of columns IB, IIB, IVA, VA, VB, IA and IIA of the periodic table of the elements.

4. The process of claim 3, wherein the anion is used in the form of the corresponding hydrogen acid.

5. The process of claim 1, wherein said additive is at least one of said metal cation of any metal of columns IB, IIB, IVA, VA and VB of the periodic table of the elements.

6. The process of claim 5, wherein the metal cation is selected from the group consisting of Cu, Ag, Cd, Hg, Sn, Pb, Sb, Bi and Ta.

7. The process of claim 6, wherein the metal cation is Pb or Ta.

8. The process of claim 5, wherein the metal cation is used in the form of an oxide or a salt.

9. The process of claim 1, wherein the anion is used in the form of a corresponding hydrogen acid or a halide of any metal of columns IB, IIB, IVA, VA, VB, IA and IIA of the periodic table of the elements.

10. The process of claim 9, wherein the anion is used in the form of the corresponding hydrogen acid.

11. The process of claim 1, wherein the total pressure is between 5 and 30 bar.

12. The process of claim 1, wherein the catalyst metal is used in the form of the metal, an oxide or a salt of the metal, or in the form of a mixture thereof.

13. The process of claim 1, wherein the catalyst is deposited on a support selected from the group consisting of charcoal, silica and alumina.

14. The process of claim 1, wherein less than 10% by weight of catalyst is used, expressed as metal relative to the aliphatic perfluoroacid.

15. The process of claim 1, wherein the aliphatic perfluoroacid used is trifluoroacetic acid of the formula $CF_3COOH$.

16. The process of claim 1, wherein the catalyst is based on a metal selected from the group consisting of ruthenium and rhodium.

17. The process of claim 1, wherein the total pressure is between 20 and 50 bar.

18. The process of claim 1, wherein the reaction is conducted at a temperature between 20° and 200° C.

19. The process of claim 1, wherein the reaction is conducted at a temperature between 120°–150° C.

20. The process of claim 1, wherein said additive is at least one of said metal cation of any metal of columns IB, IIB, IVA, VA and VB of the periodic table of the elements.

21. The process of claim 21, wherein the metal cation is selected from the group consisting of Cu, Ag, Cd, Hg, Sn, Pb, Sb, Bi and Ta.

22. The process of claim 21, wherein the metal cation is Pb or Ta.

23. The process of claim 1, wherein said halide anion is selected from the group consisting of hydrogen chloride and hydrogen iodide.

24. The process of claim 1, wherein the additive is a metal cation of any metal columns IB, IIB, IVA, VA and VB of the periodic table of the elements.

25. The process of claim 24, wherein the metal cation is selected from the group consisting of Cu, Ag, Cd, Hg, Sn, Pb, Sb, Bi and Ta.

26. The process of claim 24, wherein the metal cation is selected from the group consisting of Ag, Cd, Hg, Pb, Sb, Bi and Ta.

27. The process of claim 24, wherein the metal cation is Cu or Sn.

28. The process pf claim 1, wherein the additive is a halide anion.

29. The process of claim 28, wherein the additive is iodide or chloride.

30. The process of claim 28, wherein the additive is a fluoride.

31. The process of claim 1 wherein the halide anion is selected from the group consisting of chloride, bromide and iodide.

* * * * *